United States Patent
Nielsen et al.

(10) Patent No.: US 8,858,507 B2
(45) Date of Patent: Oct. 14, 2014

(54) CAP LOCK

(75) Inventors: Ole Christian Nielsen, Hillerød (DK); Claus Cornelius Jespersen, Copenhagen N (DK)

(73) Assignee: Novo Nordisk A/S, Bagsvaerd (DK)

( * ) Notice: Subject to any disclaimer, the term of this patent is extended or adjusted under 35 U.S.C. 154(b) by 255 days.

(21) Appl. No.: 13/254,342

(22) PCT Filed: Mar. 2, 2010

(86) PCT No.: PCT/EP2010/052617
§ 371 (c)(1),
(2), (4) Date: Mar. 19, 2012

(87) PCT Pub. No.: WO2010/100145
PCT Pub. Date: Sep. 10, 2010

(65) Prior Publication Data
US 2012/0165745 A1     Jun. 28, 2012

Related U.S. Application Data

(60) Provisional application No. 61/158,910, filed on Mar. 10, 2009.

(30) Foreign Application Priority Data

Mar. 3, 2009 (EP) .................................... 09154255

(51) Int. Cl.
| A61M 5/00 | (2006.01) |
| A61M 5/31 | (2006.01) |
| A61M 5/32 | (2006.01) |
| A61M 5/178 | (2006.01) |
| A61M 5/34 | (2006.01) |

(52) U.S. Cl.
CPC .............. *A61M 5/3202* (2013.01); *A61M 5/34* (2013.01); *A61M 5/3293* (2013.01); *A61M 5/3213* (2013.01)

USPC ...... 604/192; 604/162; 604/164.08; 604/240; 604/263

(58) Field of Classification Search
USPC ............ 604/192, 164.08, 162, 263, 240–249; 606/181–183
See application file for complete search history.

(56) References Cited

U.S. PATENT DOCUMENTS

| 3,021,942 A | * | 2/1962 | Hamilton | 206/365 |
| 5,741,236 A | * | 4/1998 | Kakiuti | 604/192 |
| 5,941,857 A | * | 8/1999 | Nguyen et al. | 604/263 |

FOREIGN PATENT DOCUMENTS

| EP | 279583 A2 | 8/1988 |
| EP | 364839 A1 | 4/1990 |
| EP | 1466638 A2 | 10/2004 |
| WO | 92/13585 A1 | 8/1992 |
| WO | 2004/004812 A1 | 1/2004 |
| WO | 2006/032385 A1 | 3/2006 |
| WO | 2008/077706 A1 | 7/2008 |

* cited by examiner

*Primary Examiner* — Emily Schmidt
*Assistant Examiner* — Lauren M Peng
(74) *Attorney, Agent, or Firm* — Wesley A. Nicolas; Reza Green; Richard W. Bork

(57) ABSTRACT

A needle assembly for a medical device comprising a needle cannula which is mounted in a hub connectable to a medical device, and which needle assembly comprises releasable locking means which co-operates with the connection means of the hub such that the needle cap is locked to the hub when the releasable locking means is not released. Once the locking means is released by activation of the connection means, the needle cap is unlocked from the hub. The activation of the locking means is preferably done automatically when the needle assembly is attached to the medical device.

8 Claims, 1 Drawing Sheet

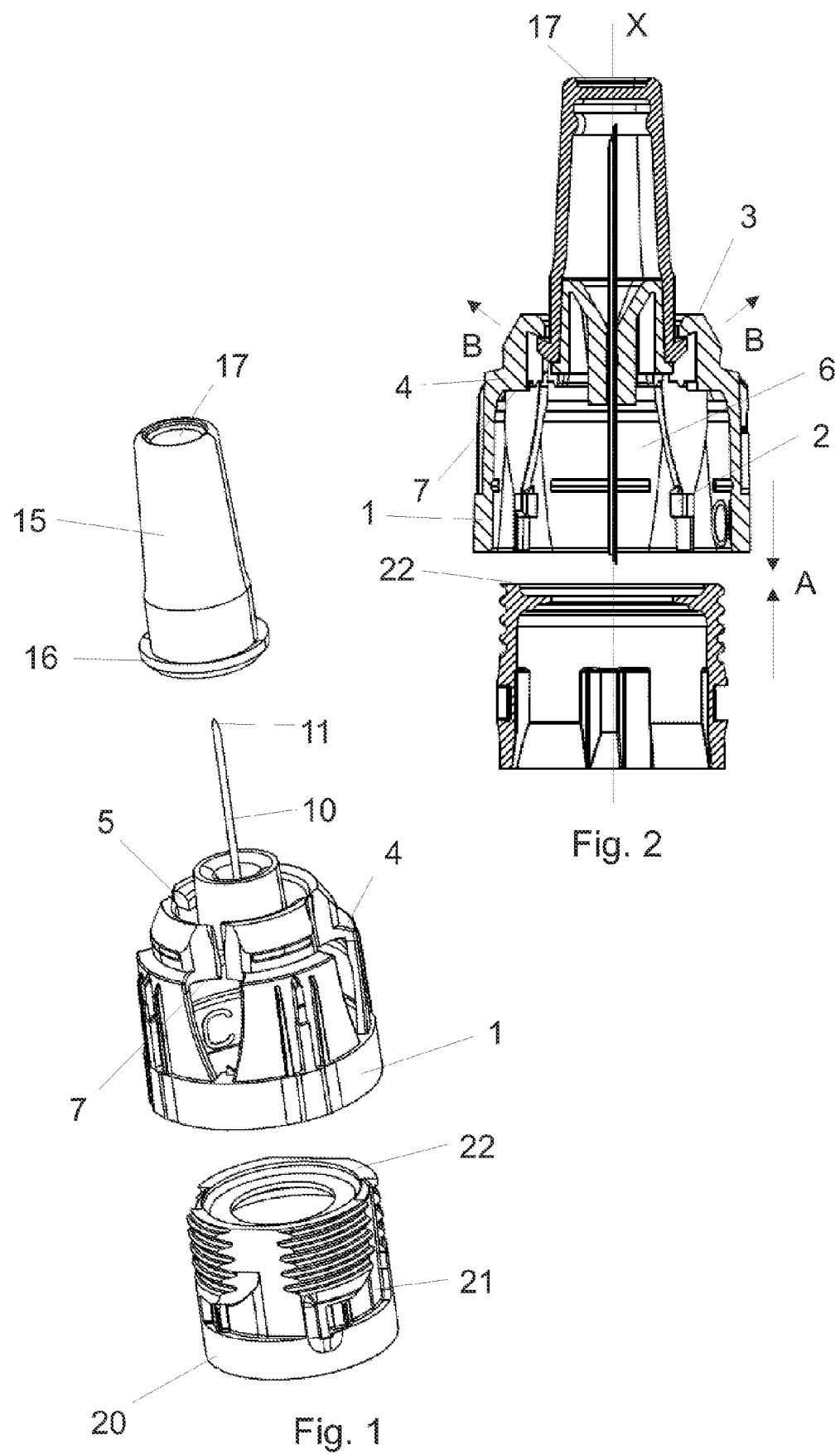

CAP LOCK

CROSS-REFERENCE TO RELATED APPLICATIONS

This application is a 35 U.S.C. §371 national stage application of International Patent Application PCT/EP2010/052617 (published as WO 2010/100145), filed Mar. 2, 2010, which claimed priority of European Patent Application 09154255.5, filed Mar. 3, 2009; this application further claims priority under 35 U.S.C. §119 of U.S. Provisional Application 61/158,910, filed Mar. 10, 2009.

THE TECHNICAL FIELD OF THE INVENTION

The invention relates to a needle assembly for a medical device and especially to a pen needle assembly having a lockable inner cap.

DESCRIPTION OF RELATED ART

People suffering from diabetes often have to inject themselves with insulin at a daily basis. For this purpose a great number of different pen systems have been developed over the last 30 years. Common for pen injectors is that they contain a container or cartridge containing the liquid drug to be injected. In order to transfer the liquid drug from the injection pen and into the body of the patient a pen needle assembly is used. Such pen needle assemblies have a needle cannula with a non-injection end which penetrates into the cartridge when the pen needle assembly is attached to the injection pen and a patient end that enters into the body of the patient during injection to create liquid communication between the inner of the cartridge and the patient. A pen needle assembly further comprises a hub carrying the cannula and which hub is usually provided with means for attaching the pen needle assembly to the injection pen.

Such pen needle assemblies are typically disposable and are normally discarded after one single use. The problem presented by the disposal of a pen needle assembly, and indeed, by any handling of the pen needle assembly, is the potential risk of being injured by any of the sharp ends of the needle cannula. This is particular dangerous when following after the penetration of a patients skin since the needle cannula then may be contaminated and therefore capable of spreading diseases such as hepatitis and HIV.

WO 2008/077706 discloses a safety pen needle assembly for an injection device in which a biasing safety shield is telescopically movable relatively to the needle cannula in order to protect a user against accidental needle injuries. The telescopic movement of the safety shield can be obstructed by a locking element which is switched between an obstructing position and a non-obstructing position by the injection device such that the safety shield is free to slide axially when the needle assembly is mounted on the injection device and prevented from sliding when the needle assembly is dismounted from the injection device.

U.S. Pat. No. 5,941,857 disclose a standard pen needle comprising a hub attachable to an injection device. In the centre of the hub the needle cannula is glued to the hub. The patient end of the needle cannula is covered by a removable inner cap, and the entire needle assembly including the inner cap is secured in a container which is usually sealed at its open end and sterilized. After an injection has been performed, the inner cap is pushed into the back-end of the needle hub where a flange (23) on the inner cap snaps behind a locking ring (35) thereby irreversible locking the inner cap to the hub and preventing a user from gaining access to the non-patient end of the needle cannula.

Another standard pen needle assembly is disclosed in EP 279,583. The patient end of this needle cannula is also covered by an inner cap, and the hub carrying the needle cannula and the inner cap is concealed in a sterile container which is sealed at the open end.

Once the hub of the pen needle assembly has been attached to the injection device such that the non-patient end has penetrated into the cartridge, the user removes the inner cap e.g. by use of the fingers or by using a tool as described in WO 2006/032385.

When handling such pen needle assembly both prior to the injection and after the injection, the inner cap can be easily removed thereby exposing the patient end of the needle cannula which can result in accidental needle stick injuries.

DESCRIPTION OF THE INVENTION

It is an object of the present invention to provide a needle assembly for a medical device which increases the safety for people handling such needle assemblies both prior to and especially after an injection.

Since the releasable locking means cooperates with the connecting means, the position of the locking means is determined by the activation of the connecting means. In one embodiment the needle cap is prevented from being removed from the needle hub due to the locking mechanism. Due to the presence of releasable locking means cooperating with the connecting means it prescribes an active interaction with the connecting means before the needle cap can be removed from the hub. This interaction can be a physical action performed manually by the user, or it can be an automated action performed as a result of a different action, e.g. in a preferred embodiment, the mounting of the needle assembly on a medical device automatically activates the locking means. When the needle cap is physically locked to the needle hub it is prevented that it accidentally becomes separated from the hub, and people are therefore better protected against accidental needle stick injuries when handling the needle assembly according to the present invention.

In a broader understanding, the needle assembly can be any kind of invasive needle e.g. a catheter or an inserter needle for a sensor or the like.

In an automated embodiment, the releasing means cooperates with the connecting means, such that when a user connects the needle assembly to an object, such as a drug delivery device, the connecting means is activated and the locking means is released such that the needle cap can be removed.

In an embodiment, the locking means is made integral with the hub e.g. by moulding the hub and the arms as one single piece. At least one of the arms preferably engages with the needle cap and is released once the needle hub is secured to a drug delivery device. "Arms" must be understood in the absolute broadest form as elements able to grip the needle cap.

According to an embodiment of the present invention, a system comprising a drug delivery device and a needle assembly further comprises a needle cap locked to a hub by a releasable lock. When in a non-use situation, the needle cap is locked to the needle hub thereby protecting a person handling the needle assembly. However, when the needle hub is attached to a drug delivery device the releasable lock is operated to unlock the needle cap which can thereafter be removed.

The locking means preferably comprises a number of arms or similar elements made integral with the needle hub and which arms are activated by the drug delivery device to shift between a first position in which they lock the needle cap to the needle hub and a second position in which the arms no longer engages with the needle cap whereby a user can remove the needle cap. The shift between the two positions is not necessarily an abrupt movement but can be graduate as the needle hub and the device is connected or separated.

Any number of arms can be used, and the number of arms actually engaging the needle cap can be lower than the actual number of arms, since some arms can be used only for guiding the needle cap. However, at least one arm have to engage with the needle cap.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid. An injection needle usually comprises a "needle cannula" and a "hub". The term "Needle Cannula" is used to describe the actual conduit performing the penetration of the skin during injection. A needle cannula is usually made from a metallic material and connected to a hub to form a complete injection needle, also often referred to as a "needle assembly". A needle cannula could however also be made from a polymeric material or a glass material. The needle cannula is mounted in a "hub", which also carries the connecting means for connecting the injection needle to an injection apparatus and is usually moulded from a suitable thermoplastic material. The "connecting means" could as examples be a luer coupling, a bayonet coupling, a threaded connection or any combination thereof, e.g. a combination as described in EP 1,536,854. "Cartridge" is the term used to describe the container containing the drug. Cartridges are usually made from glass but could also be moulded from any suitable polymer. A cartridge or ampoule is preferably sealed at one end by a pierceable membrane which can be pierced e.g. by an injection needle. The opposite end is closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 1 Show an exploded view of the needle assembly,

FIG. 2 Show a cross sectional view of the needle assembly prior to mounting on an injection device.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the needle cannula penetrating the patient whereas the term "proximal end" is meant to refer to the opposite end pointing away from the patient in a situation of use.

FIGS. 1 and 2 discloses a needle hub 1 provided with interior coupling means 2 such as a thread or one or more protrusions for a bayonet coupling as described in EP 1,536, 854. These coupling means 2 co-operates with similar engaging means 21 on the distal end of the injection device 20.

Although the term "injection device" is used through out this application, a Penfill® equipped with an adapter top or a similar coupling interface to fit into a Novo Nordisk pen system according to U.S. Pat. No. 5,693,027 or a similar container with drug provided with connecting means for a needle assembly is also considered to fall under this term, as the Penfill® or the similar container becomes part of the injection device in a situation of use.

A needle cannula 10 is secured to the needle hub 1 such that a sharp patient end 11 protrudes in the distal direction. This sharp patient end 11 is shielded by a removable needle cap 15. The needle cap 15 is at its proximal end provided with a circumferential protrusion 16. Although, the needle assembly is depictured with a double-pointed needle cannula the back-end of the needle cannula is not a necessity for the described invention.

The needle hub 1 has a number of arms 3 pointing in the distal direction. These arms 3 are secured to the hub 1 through a number of flexible hinges 4. Preferably, the hub 1, the arms 3 and the hinges 4 are moulded as one component.

The arms 3 are distally provided with hooks 5 which engage with the circumferential protrusion 16 on the needle cap 15. In order to enhance the grip between the hooks 5 and the circumferential protrusion 16, one or both of them can be shaped with an inclined surface as disclosed in FIG. 2.

The flexible hinges 4 are shaped such that the hooks 5 on the arms 3 cave slightly inwardly toward a centre axis X. In this position the hooks 5 engage behind the circumferential protrusion 16 of the needle cap 15 and prevent the needle cap 15 from being removed.

When the adapter-top or the injection device 20 is inserted into the connecting area 6 of the needle hub 1, being the area 6 into which the injection device 20 is inserted when the needle assembly and the injection device 20 are attached to each other, the distal end 22 of the injection device 20 abuts with the proximal end 7 of the arms 4. The arrow A in FIG. 2 indicates the direction in which the adapter top or the injection device 20 and/or the needle assembly is moved during attachment of a needle assembly. Due to the abutment between the distal end 22 of the injection device 20 and the proximal end 7 of the arms 3, the arms 3 will bent outward as indicated with the arrows B in FIG. 2.

With the arms 3 in this deflected position, the user can remove the needle cap 15. After use, e.g. when the needle assembly has been removed from the adapter top or injection device 20, the user can mount the needle cap 15 by simply pressing it back onto the hub 1, and the needle cap 15 will once again be locked to the hub 1. The needle cap 15 could also be replaced prior to removing the needle assembly from the injection device in which situation it will automatically become locked once the user removes the needle assembly from the injection device.

In order to enhance this deflection, the arms 3 could on their proximal end surface 7 be provided with not-shown protrusions which would then abut the distal end 22 of the injection device 20 during mounting of the needle assembly.

If a double pointed needle cannula 10 is used as disclosed in FIG. 2, it would be an advantage if the needle cap 15 was provided with a hardened top 17, such that a user—after use—can bend the back-end of the double pointed needle 10 by use of the needle cap 15, Since needle assemblies are usually delivered to the user in a rigid and sterile container which are shaped as a tool for assisting the user in mounting the needle assembly on to the injection device, the outer container could be provided with a hardened top for bending the back-end of the needle cannula 10.

Some preferred embodiments have been shown in the foregoing, but it should be stressed that the invention is not limited to these, but may be embodied in other ways within the subject matter defined in the following claims.

The invention claimed is:

1. A needle assembly for an injection device (20), comprising:
    a needle hub (1) having connecting means (2) for connecting the needle hub (1) to the medical device (20),
    a needle cannula (10) secured to the hub (1) and having a patient end (11),
    a removable needle cap (15) adapted to cover the patient end (11) of the needle cannula (10) in a non-use situation, wherein the needle assembly further comprises releasable locking means (3, 4) which prevents the needle cap (15) from being removed from the needle hub (1) and wherein the releasable locking means (3, 4), when released, allows the needle cap (15) to be removed from the needle hub (1), wherein the connecting means (2) is activated by being connected to the injection device and wherein activation of the connecting means releases the releasable locking means to allow the cap to be removed and wherein the locking means (3, 4) is integrated with the needle hub (1).

2. A needle assembly according claim 1, wherein the releasable locking means (3, 4) comprises a number of arms (3).

3. A needle assembly according to claim 2, wherein, at least one of the arms (3) engages the needle cap (15) thereby locking the needle cap (15) to the needle hub (1).

4. A medical injection device and needle assembly system comprising:
    an injection device connectable to a needle assembly and a needle assembly connectable to the injection device (20),
    wherein the needle assembly comprises a needle cannula (10) having a patient end (11) and wherein the needle cannula (10) is mounted to a needle hub (1), the needle hub (1) having connecting means (2) adapted for connecting the hub (1) to an injection device (20), and wherein a needle cap (15) is adapted to cover the patient end (11) of the needle cannula (10), wherein, the system further comprises releasable locking means (3, 4) co-operating with the connecting means (2) to lock the needle cap (15) to the needle hub (1) and wherein the releasable locking means (3, 4) is activated to unlock the needle cap (15) when the connecting means (2) of the needle assembly is connected to a medical injection device (20) and wherein the releasable locking means (3, 4) is integral with the needle hub (1) and comprises one or more arms (3) engaging the needle cap (15) and that at least one arm (3) can be shifted between a locking position and a non-locking position by activation from the injection device (20).

5. A medical device and needle assembly system comprising:
    a medical injection device (20) connectable to a needle assembly and a needle assembly connectable to the medical device (20),
    wherein the needle assembly comprises a needle cannula (10) having a patient end (11) and wherein the needle cannula (10) is mounted to a needle hub (1), the needle hub adapted for connecting the hub (1) to the medical device (20), and wherein a needle cap (15) is adapted to cover the patient end (11) of the needle cannula (10), wherein, the system further comprises releasable lock that cooperates with the needle hub so that when the hub is connected to the injection device it allows the needle cap to be removed but prevents removal of the needle cap when the hub is not connected to the injection device.

6. A needle assembly for an injection device (20), comprising:
    a needle hub (1) having a connector that allows the connecting of the needle hub (1) to the medical device (20),
    a needle cannula (10) secured to the hub (1) and having a patient end (11),
    a removable needle cap (15) adapted to cover the patient end (11) of the needle cannula (10) in a non-use situation, wherein the needle assembly further comprises releasable lock that prevents the needle cap (15) from being removed from the needle hub (1) and wherein when the releasable lock is activated to release, the needle cap (15) is removable from the needle hub (1) and wherein the releasable lock is activated to unlock when the needle assembly is connected to the injection device, wherein the activation occurs by the mounting of the hub onto the injection device.

7. The needle assembly of claim 6, wherein the lock is integrated with the needle hub.

8. A needle assembly for an injection device, the assembly comprising:
a needle cannula;
a hub in which the cannula is mounted, the hub being adapted to be mountable on an injection device;
a cap mountable on the needle assembly and wherein when mounted the cap covers an end of the cannula; and wherein when the cap is not removable from the needle assembly unless the hub is mounted on an injection device; and wherein when the hub is mounted on an injection device the cap is freely removable; and wherein the cap is automatically locked to the hub when the hub is removed from the injection device.

* * * * *